United States Patent
Lawrence et al.

(10) Patent No.: US 7,255,832 B2
(45) Date of Patent: Aug. 14, 2007

(54) ICONIC COLORIMETRIC TEST DEVICE WITH REDUCED SUSCEPTIBILITY TO FALSE POSITIVE AND FALSE NEGATIVE READINGS

(75) Inventors: Paul J. Lawrence, Pacific Grove, CA (US); Aulena Chaudhuri, San Jose, CA (US)

(73) Assignee: Quidel Corporation, San Diego, CA (US)

( * ) Notice: Subject to any disclaimer, the term of this patent is extended or adjusted under 35 U.S.C. 154(b) by 0 days.

(21) Appl. No.: 10/944,283

(22) Filed: Sep. 17, 2004

(65) Prior Publication Data

US 2005/0070021 A1 Mar. 31, 2005

Related U.S. Application Data

(60) Provisional application No. 60/504,066, filed on Sep. 19, 2003.

(51) Int. Cl.
*G01N 21/01* (2006.01)
*G01N 21/25* (2006.01)
*G01N 31/22* (2006.01)

(52) U.S. Cl. .......................... 422/56; 422/57; 422/58; 422/61

(58) Field of Classification Search ............ 422/55–58, 422/61
See application file for complete search history.

(56) References Cited

U.S. PATENT DOCUMENTS

| | | | |
|---|---|---|---|
| 3,620,676 A * | 11/1971 | Ward ........................... 422/57 |
| 4,523,852 A * | 6/1985 | Bauer .......................... 356/421 |
| 4,683,209 A * | 7/1987 | Ismail et al. .................. 436/14 |
| 4,916,056 A | 4/1990 | Brown, III et al. |
| 4,981,653 A * | 1/1991 | Marino ......................... 422/56 |
| 5,008,080 A | 4/1991 | Brown, III et al. |
| 5,132,085 A * | 7/1992 | Pelanek ........................ 422/55 |
| 5,541,059 A * | 7/1996 | Chu .............................. 435/5 |
| 5,660,790 A | 8/1997 | Lawrence et al. |
| 5,897,834 A | 4/1999 | Lawrence et al. |
| 5,910,447 A | 6/1999 | Lawrence et al. |
| 6,099,801 A | 8/2000 | Lawrence et al. |
| 6,113,856 A | 9/2000 | Lawrence et al. |
| 6,200,817 B1 | 3/2001 | Lawrence |
| 6,284,198 B1 | 9/2001 | Kirollos et al. |
| 6,406,441 B1 * | 6/2002 | Caillouette .................. 600/584 |
| 6,855,561 B2 * | 2/2005 | Jerome et al. .............. 436/514 |

* cited by examiner

*Primary Examiner*—Arlen Soderquist
(74) *Attorney, Agent, or Firm*—Townsend and Townsend and Crew, LLP

(57) ABSTRACT

Laminated test devices in which positive results are detected by the appearance of a symbol on the surface of the device due to a color change in an indicator in the device are improved by placing the indicator lamina on one side of a light-transmissive substrate sheet and a pigment lamina on the other side, the indicator lamina forming the icon and the pigment lamina forming the background, the pigment being the color of the indicator prior to the color change. This arrangement reduces false positive readings by obscuring the outlines of the symbol prior to the color change. False negative readings are reduced by further changes in the arrangement of the laminae.

17 Claims, 5 Drawing Sheets

ICONIC COLORIMETRIC TEST DEVICE WITH REDUCED SUSCEPTIBILITY TO FALSE POSITIVE AND FALSE NEGATIVE READINGS

CROSS-REFERENCE TO RELATED APPLICATION

This application claims benefit from U.S. Provisional Patent Application No. 60/504,066, filed Sep. 19, 2003, the contents of which are incorporated herein by reference in their entirety.

BACKGROUND OF THE INVENTION

1. Field of the Invention

This invention resides in the field of test devices for clinical use that provide visual readouts, and is particularly concerned with test devices that utilize a calorimetric indicator to display an icon or symbol indicating either the presence or absence of a particular substance in a sample, a high or low concentration of a substance, a high or low pH, or any such indication of either a desired or undesired condition of the sample.

2. Description of the Prior Art

Test devices that produce visually detectable plus signs to indicate the presence of bacterial vaginosis in a sample of vaginal fluid are disclosed in the following United States patents (inventors: Paul J. Lawrence et al.): U.S. Pat. No. 5,660,790, issued Aug. 26, 1997; U.S. Pat. No. 5,897,834, issued Apr. 27, 1999; U.S. Pat. No. 5,910,447, issued Jun. 8, 1999; U.S. Pat. No. 6,099,801, issued Aug. 8, 2000; U.S. Pat. No. 6,113,856, issued Sep. 5, 2000; and U.S. Pat. No. 6,200,817, issued Mar. 13, 2001. Two distinct tests are disclosed in these patents: a pH test of vaginal fluid in which a pH of 4.7 or greater serves as one indication of an infection, and an amine test in which the presence of volatilizable amines serves as another indication of an infection. The devices in these patents are laminated test cards and the tests are conducted by applying a specimen of vaginal fluid to the surface of a card with a swab and checking the card for the appearance of symbols on the card surface. In each of these two tests, a negative test result appears as a "minus" sign formed by a single horizontal bar and a positive result appears as a "plus" sign formed by two bars crossing at right angles. The plus sign is formed by two separately operable but intersecting bars: one horizontal (the positive control); and, the second vertical (the test response). The horizontal bar thus appears regardless of the outcome of the test, and thereby serves as a positive control indicating that the indicator that causes the color change in both bars is functioning properly. Thus, if no bar at all appears after application of a sample, the test device is deemed not usable and should be discarded; the appearance of a single bar (a "minus" sign) means that the device is functional and the test result is negative; and the appearance of both bars (to form the "plus" sign) indicates that the device is functional and the test result is positive.

Plus and minus signs are also produced by the test devices disclosed in U.S. Pat. No. 4,916,056, issued Apr. 10, 1990, and U.S. Pat. No. 5,008,080, issued Apr. 16, 1991, both to inventors William E. Brown, III, et al. The tests in these patents involve immunological binding rather than pH changes, but like the Lawrence et al. patents, the tests results are displayed as a plus sign formed when two separately operable but intersecting bars become visible and a minus sign formed from when only one of the two bars becomes visible. All patents in this and the preceding paragraph are incorporated herein by reference in their entirety.

Licensed physicians and laboratory technicians find products like these useful and efficient because of their compact nature and their simple visual readout. Since they are easy to use, the devices are also attractive for consumers and other individuals who are not clinically trained. This is particularly true of the Lawrence et al. devices where the test procedures consist of simply applying a swab of the sample to the surface of the device, and watching the device to see what symbols appear. In some cases, however, users, particularly untrained individuals, may read the devices incorrectly, reporting results that are either false negatives or false positives.

One source of an incorrect reading arises from the independent responses of the two independent, separable but intersecting bars and the fact that the response of each bar can vary to some degree with the amount of sample applied to the device or the amount or concentration of analyte in the sample. Slight differences in color intensity between the two intersecting bars can prompt the user to treat one bar as a color comparator for the other, and thereby wait for the color of the vertical bar to precisely match that of the horizontal bar before declaring a positive result. A positive result can thus be interpreted as negative (i.e., a false negative).

Another source of an incorrect reading occurs when the outlines of the intersecting horizontal and vertical bars are visible, even when only faintly so, before any color change has occurred. This problem can occur with any iconic readout, the terms "iconic" and "icon" referring herein to any graphical symbol whose form suggests its meaning. In the case of the Lawrence et al. and Brown et al. devices, the icon is either a minus sign indicating a negative result when only one bar appears or a plus sign indicating a positive result when both bars appear. The icon can also be a unitary plus sign that appears only as a whole and lacks the capability of allowing only the minus sign portion to appear. Icons of other forms or shapes will be readily apparent. With any of these icons, incorrect readings can arise from the construction of the device, which typically involves several laminae one or more of which forms the outlines of the icon. In some cases, for example, the icon is formed by a channeling lamina with an icon-shaped opening, overlying an indicator lamina that extends over the full lateral dimensions of the device, or at least beyond the boundaries of the opening. The channeling lamina permits the sample (and any analyte present) to contact only the portion of the indicator that is directly below the opening. Even if the channeling lamina is completely transparent, the edges of the opening can be visible to one who looks closely at the device, since the light reflectivity of the channeling lamina may differ from that of the indicator lamina. In other cases, the icon is formed by the indicator lamina itself which is in the shape of the icon and rests above any underlying layers. Although the filed behind the icon is the same color as the icon (prior to the test), the edges of the icon are faintly visible due to the difference in height, even though that difference may be very small. To the unskilled or untrained user, this visibility can suggest a positive test result when the result is actually negative (i.e., a false positive result). The thickness difference can be minimized or eliminated by depositing a material in the areas adjacent to the icon, using a material that does not change color upon contact with either the sample or the analyte. The icon and the surrounding material will then be of different chemical compositions, however. This by itself can produce enough of a color difference, however slight, to make the borders between the two visually distinguishable. Furthermore, if there is a risk of the indicator diffusing into the surrounding material and thereby obscuring the readout, precautions or structural features to prevent this from happening can also make the outline visible.

SUMMARY OF THE INVENTION

It has now been discovered that false readings of icons on test devices such as those described above can be reduced or eliminated by constructing the device as a laminate that includes among its laminae a light-transmissive, liquid-impermeable lamina coated on one side with an indicator lamina and on the other side with a pigment lamina that is the same color as the indicator before the color change that indicates a positive test result. The light-transmissive, liquid-impermeable lamina is also referred to herein as a "substrate sheet" since it can serve as a convenient base for applying the other laminae on both sides and since it is typically flat and thin. The icon is formed either by a channeling lamina over the indicator lamina or by limiting the size and shape of the indicator lamina so that it forms the icon by itself. In either case, the pigment lamina extends beyond the icon area, and preferably over the icon area as well. As described herein, the test device contains a delineated test region that contains the colored areas, including the icon area that changes color upon the occurrence of a positive test result and the non-changing area (or field) surrounding the icon area that makes the icon substantially invisible until the icon area changes color. The icon area is thus a restricted area within, and smaller than, the test area. The test area itself can extend across the entire length and width of the device, although in preferred embodiments, the test area will be a smaller area covering only a portion of the total area of the device.

In further preferred embodiments of the invention, the test device includes a positive control area within the test area but spatially separated from, and significantly smaller than, the icon area. In these embodiments, the positive control serves the same purpose as the positive control on the devices disclosed in the Lawrence et al. and Brown et al. patents referenced above but does not form part of the positive test result icon. In addition to their spatial separation, the positive control and the test icon preferably differ in size and shape, with the separation, the size, and the shape differences tending to eliminate any confusion in the mind of the user between a control signal and a positive test signal.

It has also been discovered that a test for volatile amines when performed on a sample of vaginal fluid, utilizing the color-change methodology of the Lawrence et al. patents cited above, with either the laminate arrangement disclosed in those patents or any of the laminate arrangements disclosed herein, is sufficiently indicative of bacterial vaginosis that the volatile amines test alone can replace the more traditional diagnosis based on the Amsel criteria. The Amsel criteria for bacterial vaginosis (BV) are based on a report by Amsel, R., et al., *Am. J. Med.* 74:14-22 (1983), which sets forth four criteria that collectively result in a diagnosis of BV: elevated pH (originally 4.5 or above, now 4.7 or above) of a vaginal fluid specimen, a "whiff" test (treatment of the specimen with alkali followed by an olfactory test to detect an amine odor), vaginal fluid homogeneity, and the presence of clue cells. To detect a positive result according to the Amsel criteria, the elevated pH must be met, together with at least two of the remaining three criteria. The present invention resides in the discovery that the use of the amines test alone will serve as an effective diagnosis.

Further features, embodiments, and benefits of the invention will be apparent from the description that follows.

DETAILED DESCRIPTION OF THE INVENTION AND PREFERRED EMBODIMENTS

Figure 1:
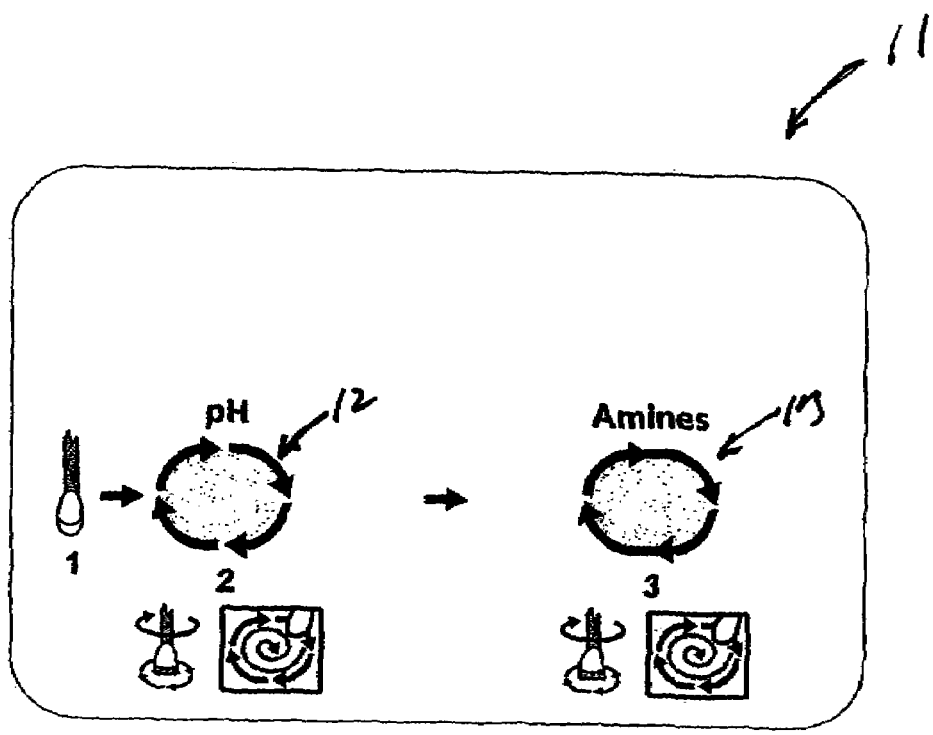
FIG. 1 is a plan view of a test device in accordance with the present invention and containing two test regions, one to determine whether a particular pH threshold has been passed in a liquid sample and the other for the presence of volatilizable amines in the sample.

In the various embodiments of this invention, the indicator lamina, also referred to herein as the "analyte indicator lamina" is one that changes color to indicate a positive test result. Samples that can be tested on the devices of this invention are liquid samples, including biological liquid samples, and a positive test result is a visually detectable color change in the indicator due to a chemical reaction between the indicator and a component of the sample. The positive test result can thus arise from the presence of a distinct species in the sample, the absence of a distinct species (i.e., a species that would otherwise inhibit the reaction), a pH of the sample that is above or below a transition point, or any such quality or characteristic of the sample that serves as an indication of a condition whose presence is sought to be determined. In many cases, the indicator in the analyte indicator lamina will be a pH indicator that will undergo a visible color change when the pH passes a transition point. Many conventional pH indicators can be used, the choice of course depending on the transition point and the particular analyte. The lamina itself will preferably consist of a hydrophilic fluid-permeable polymer that serves as a matrix for an impregnated indicator.

The pigment lamina is a lamina that is substantially indistinguishable colorimetrically from the analyte indicator lamina prior to any change occurring in the analyte indicator lamina upon application of the sample. Accordingly, the pigment lamina can be of the same composition as the analyte indicator lamina and prevented from changing color by the substrate sheet which is located between the analyte lamina and the pigment lamina, thereby keeping the two out of contact. The substrate sheet will be impermeable to the sample liquid so that the sample will not diffuse through the sheet. The pigment lamina can also be prevented from contact with the sample by placing a protective sealing lamina over the pigment lamina. Alternatively, and preferably, the pigment lamina is a colored ink that is chemically distinct from the indicator lamina and non-reactive with the analyte, or at least undergoes no reaction or color change upon contact with the sample, regardless of whether the sample contains or does not contain the analyte. Common commercial inks or ink combinations can be used.

The substrate sheet separating the analyte indicator lamina from the pigment lamina, in addition to being impermeable to the liquid sample, is light-transmissive to render the pigment lamina visible through the sheet, i.e., from the indicator side of the sheet. Preferably, the substrate sheet is transparent and colorless. A presently preferred material for the substrate sheet is a polyethylene terephthalate fill such as MYLAR® (Du Pont de Nemours & Co., Wilmington, Del., USA). In many cases, a coating over the substrate sheet can improve the adherence of the laminae that are applied over it, particularly when the pigment and indicator laminae are susceptible to damage during the handling of the device as it is being manufactured or during use. This type of damage can occur, for example, when the laminae are applied as solutions in solvents that do not penetrate the substrate sheet. Laminae that are deposited using aqueous and alcohol solvents, for example, do not adhere well to MYLAR. A preferred coating material that can improve this adherence is polyamide.

The icon is formed by restricting the color change in the analyte indicator lamina to a restricted area within the test region. This is accomplished either by the use of a channeling lamina overlying the analyte indicator lamina, the channeling lamina containing an icon-shaped opening to expose an icon-shaped area of the analyte indicator lamina, or by forming the analyte indicator lamina itself in the shape of the icon, leaving the adjacent areas free of indicator. When a channeling lamina is used, the channeling lamina is preferably transparent. As noted above, the icon can assume any shape or form, preferably one that conveys the message of a positive test result to the user. A plus sign is preferred, particularly one that, once visible due to the color change, is fully surrounded by areas that are the same color as the icon before the color change.

In embodiments that contain a positive control in addition to the test icon, the positive control as noted above is preferably spatially separated from the test icon and of a different size and shape. The positive control is itself an icon, and in embodiments having a plus sign-shaped test icon, a convenient positive control icon is a circular dot of a diameter substantially smaller than the plus sign, in keeping with the secondary role of the positive control. The positive control icon is itself an indicator, but one that changes color upon contact with any sample regardless of whether the sample contains the analyte (or the absence of the analyte, or other chemical condition) that will produce the color change in the test icon. Prior to application of the sample, the positive control icon will display a color that is identical both to that of the test icon and to that of the background in the test region. The color change in the positive control icon is preferably the same as that in the test icon, although produced in a different manner to respond to the sample rather than the analyte. The difference may be a different transition point or any other characteristic that will differentiate between serving as a positive control and indicating a positive test result.

The test icon and the positive control icon are preferably contained in a common test region on the test device, and the user is instructed to apply the sample over the entire test region so that both the test icon and the positive control are contacted with the sample. The preferred test region is therefore small enough that it can easily be covered with the amount of sample that can be contained in a single swab, such as a Q-tip or any other common implement that the consumer may keep in a medicine cabinet. To accommodate both icons and allow the sample to be applied by a circular motion, a convenient shape for the test area is an ellipse, an oval, or a wider bar with circular arc-shaped ends.

Further assurance of a consistent and unchanging background color beneath the test device to afford a more consistent detection of the color change in the icons, i.e., both the test icon and the positive control icon, can be achieved by the optional placement of an opaque white lamina over the entire outer side of the pigment lamina (i.e., on the side of the pigment lamina opposite the side occupied by the substrate sheet). This is particularly useful when the pigment lamina, the analyte indicator lamina, and the positive control allow small amounts of light to pass.

It has also been found that when the pigment lamina is formed from the same material as the analyte indicator lamina, the background color will appear more consistent with that of the test icon (prior to a color change in the icon), and the icon outlines less visible, when an outer transparent coating layer is placed over the pigment lamina, i.e., once pigment material is applied to the bottom surface of the substrate sheet, the outer transparent coating is applied over the pigment material. Although the inventors do not intend to be bound by this explanation, it is believed that the solvent system for the outer transparent coating, which in the preferred embodiments herein is n-propanol, penetrates the pigment layer to a small degree and produces a slight color change that further obscures the outlines of the test icon.

As a still further option when the pigment lamina is formed from the same material as the analyte indicator lamina, the pigment lamina can be protected from damage or color change due to exposure to or contact with objects or liquids during handling by a protective coating. This coating can be the outermost lamina on the bottom surface of the device, and can be of the same material as the channeling lamina or any other inert, non-porous lamina of the device. The protective lamina can be light-transmitting or opaque. Polyamide is a preferred material for this lamina.

Two examples of tests that can be performed on devices that meet the above description are the pH test and the amine test that are described in the Lawrence et al. patents referenced above. These are two distinct tests that are performed on samples of vaginal fluid and are used in the diagnosis of bacterial vaginosis.

pH Test

The pH test indicates whether the sample has a pH of 4.7 or higher, as one of several indications of bacterial vaginosis. The analyte indicator lamina in the pH test is a deposited material that includes a combination of (i) a pH indicator with an ionizable phenol group and a negatively charged group and (ii) a polymer matrix the polymer of which contains quaternary ammonium groups which immobilize the indicator in the matrix. A wide variety of pH indicators with ionizable phenol groups and negatively charged groups are known. Preferred groups of negative charge are sulfate and sulfonate groups. Examples of indicators with ionizable phenol groups and negatively charged groups are:

acid blue 92 (anazolene sodium, CAS No. 3861 73 2)

acid blue 29 (CAS No. 5850 35 1)

acid alizarin violet N (CAS No. 2092 55 9)

bromophenol blue (3',3",5',5"-tetrabromophenolsulfonephthalein, CAS No. 15539 9)

bromochlorophenol blue (3',3"-dibromo-5',5"-dichlorophenolsulfonephthalein, CAS No. 102185 52 4)

bromocresol green (3',3",5',5"-tetrabromo-m-cresolsulfo-nephthalein, CAS No. 76 60 8)
chlorophenol red (3',3"-dichlorophenol sulfonephthalein, CAS No. 4430 20 0)
bromocresol purple (5',5"-dibromo-o-cresolsulfonephthalein, CAS No. 115 40 2)
alizarin complexone dihydrate ((3,4-dihydroxy-2-anthraquinolyl)-methyliminodiacetic acid, CAS No. 3952 78 1)
alizarin red S monohydrate (3,4-dihydroxy-9,10-dioxo-2-anthracenesulfonic acid, sodium salt, CAS No. 130 22 3)
bromothymol blue (3',3"-dibromothymolsulfonephthalein, CAS No. 76 59 5)
brilliant yellow (CAS No. 3051 11 4)
phenol red (phenolsulfonephthalein, CAS No. 34487 61 1)
cresol red (3',3"-dimethylphenolsulfonephthalein, CAS No. 1733 12 6)
m cresol purple (2',2"-dimethylphenolsulfonephthalein, CAS No. 2303 01 7)
thymol blue (2',2"-dimethyl-3',3"-diisopropylphenolsulfonephthalein, CAS No. 76 61 9)
nitrazine yellow (2-(2,4-dinitrophenylazo)naphthol-3,6-disulfonic acid, disodium salt, CAS No. 5423 07 4)

All of these indicators are readily available from commercial suppliers. Preferred indicators are bromophenol blue, bromochlorophenol blue, bromocresol green, bromocresol purple, bromothymol blue, brilliant yellow, and nitrazine yellow.

The quaternary ammonium groups in the polymer can be any such groups capable of asserting a positive charge sufficient to form an ionic attraction with the negatively charged group(s) in the indicator. Preferred quaternary ammonium groups are lower alkyl ammonium groups in which the alkyl groups are $C_1$-$C_4$ alkyl groups. Trimethylammonium groups are particularly preferred. The quantity of quaternary ammonium groups in the polymer formulation can vary widely, depending on where (i.e., at what pH value) the color transition point is intended to be. In many applications of this invention, the amount of quaternary ammonium groups will be selected to lower the mid-range transition point of the indicator by about 1.0 to about 3.0 pH units, and preferably by about 1.5 to about 2.5 pH units, with about 2.0 pH units preferred. The amount of quaternary ammonium groups can also be expressed in terms of the alkali value of the resulting polymer, i.e., the milligrams of KOH equivalent to the basicity of the quaternary ammonium groups contained in 1 g of the dry polymer. In most implementations of this invention, the alkali value will range from about 5 to about 50, with values ranging from about 15 to about 40 preferred.

The polymer forming the matrix is preferably porous (or otherwise water permeable) and hydrophilic. The hydrophilic character of the polymer arises either from the quaternary ammonium groups or from other groups on the polymer structure. Any polymer which is inert to the sample components, solid and capable of being formed into a thin layer, coating or lamina can be used. The polymer should be largely insoluble in aqueous media, particularly in vaginal fluid for those embodiments of the invention that are designed for testing vaginal fluid, and preferably transparent. Examples are acrylic polymers, particularly copolymers of acrylic and methacrylic acid esters, and diethylaminoethyl cellulose. Two presently preferred polymers that are readily available from commercial suppliers are EUDRAGIT® RL PO and EUDRAGIT® RS PO Ammonio Methacrylate Copolymers, which are copolymers of methyl, ethyl and trimethylammonioethyl esters of acrylic and methacrylic acids, as chloride salts. The quaternary ammonium groups are present on these polymers as trimethylammonioethyl esters of methacrylate units that constitute 10.4% (RL PO) or 5.6% (RS PO) by weight of the polymer. The alkali values are 28.1 and 15.2, respectively. These polymers are available from Rohm Tech Inc., Malden, Mass., USA.

The combination of nitrazine yellow and the trimethylammonioethyl esters of EUDRAGIT RL PO illustrates how different pH transition points can be achieved. The transition point of nitrazine yellow in the absence of quaternary ammonium groups is about pH 6.6. Using a liquid solution of which the polymer constitutes 25.0% and nitrazine yellow constitutes 0.2% to 0.34%, the transition point will be pH 4.7. With 25.0% polymer and 0.36% nitrazine yellow, the transition point will be pH 4.4. With 25.0% polymer and 0.4% nitrazine yellow, the transition point will be pH 4.4. With 25.0% polymer and 0.6% nitrazine yellow, the transition point will be pH 4.3. All percents are by weight.

For nitrazine yellow and EUDRAGIT RL PO, the ratio, expressed as the weight ratio of KOH equivalent in the polymer to nitrazine yellow, has a preferred range of about 1.0:1 to about 6.0:1, and a more preferred range of about 1.5:1 to about 3.5:1. For EUDRAGIT RL PO, a preferred weight ratio range of polymer to nitrazine yellow is about 50 to about 250, and more preferably about 75 to about 125. If the polymer and indicator are applied as a liquid solution, a preferred range of the polymer in the solution is about 12% to about 35%, and a preferred range of the nitrazine yellow is about 0.05% to about 1.0%, all by weight.

The indicator in the positive control icon is a pH indicator whose transition point is at least about 0.7 pH unit lower than the transition point of the test indicator. When the positive control is contacted with a liquid whose pH lies between its transition point and the transition point of the test indicator, a color change in the positive control informs the user that the indicator in the positive control is in functional condition, which is logically extended to mean that both indicators are in functional condition. A color change in the positive control also indicates that the amount of sample applied to the device was adequate. Preferably, the same color change occurs in both indicators. If the test indicator has a transition point of pH 4.7, for example, the positive control preferably has a transition point of pH 4.0 or below, and most preferably pH 3.5 or below.

An example of an indicator that is useful for the positive control when the pH indicator lamina has a transition point of 4.7 is a mixture of nitrazine yellow and bromocresol green. The weight ratio of nitrazine yellow and bromocresol green in such a mixture can vary and different ratios will produce different transition points. In general, however, best results will be obtained with a weight ratio (bromocresol green to nitrazine yellow) of about 0.05 to about 20.0, and preferably from about 0.5 to about 5.0.

The polymer and indicator combinations for both the test and positive control icons preferably form solid, thin laminae that are homogeneous, transparent, and water permeable, and that neither dissolve nor disintegrate when placed in contact with aqueous liquids. Additional components can be included in each lamina or in the composition from which the lamina is formed, for a variety of purposes. For example, a vehicle for spreading or applying the lamina components to a surface can be included, as well as drying agents, penetrants, agents to facilitate wetting of the polymer by the sample, and agents to facilitate depositing the mixture on, or adhering it to, the surface of the substrate sheet.

The substrate sheet that serves as a support for both the analyte indicator lamina and positive control can be formulated to stabilize the indicators and render them easier to apply. An example of a substrate sheet that serves these purposes is a polyethylene terephthalate film such as MYLAR® (Du Pont de Nemours & Co., Wilmington, Del., USA) coated with ethyl cellulose or a similar coating to improve the adherence of the indicators. The coating may also contain acid to further control the pH of the indicator to be deposited over the coating. Different amounts of acid may be present in different regions of the coating to assist in the independent pH control of the test indicator and the control indicator.

Although the tests and test devices of this invention can be used for testing aqueous liquids from any source, the invention will be of primary interest in biological fluids, such as urine, saliva, blood, cerebrospinal fluid, and vaginal fluid. In vaginal fluid, as indicated above, a prime example of the use of this invention is in the detection of bacterial vaginosis. Vaginal fluid can also be tested for other purposes by this invention, such as for example for the pH change (a rise from 4.5 to 7.0 and higher) accompanying the rupture of the amniotic membrane. The invention will be of interest not only in testing human fluids, but also fluids from animals, such as livestock and pets. One example is the detection of mastitis in cattle by determining whether the pH of the milk has reached or surpassed a threshold value of approximately 6.8.

Amine Test

In addition to its analyte indicator and positive control laminae, the amine test includes a solid gas-releasing lamina immediately accessible to the fluid specimen, and the analyte indicator lamina is a gas-permeable lamina that is impermeable to the aqueous liquid sample itself or to any of its components that are not in gaseous form. The gas-releasing lamina is a solid lamina of alkali that reacts with amine salts in the specimen and converts them to volatile amines. The volatilized amines then penetrate the gas-permeable analyte indicator lamina where they cause a color change in the indicator.

The terms "volatile amines" and "volatilized amines" include amines that are only slightly volatile as well as those that are sufficiently volatile to escape into the atmosphere at substantial rates. Slightly volatile amines are those that form only a thin film of gas at the liquid surface without significant amounts diffusing into the atmosphere. This thin film of gas however is sufficient to penetrate the gas-permeable indicator lamina. The choice of solid alkali for the gas-releasing lamina is not critical and can vary. In general, alkali and alkaline earth metal aluminates, carbonates and hydroxides can be used. Best results will most often be achieved with the use of either sodium aluminate, sodium carbonate, or magnesium hydroxide. Sodium aluminate is particularly preferred.

Laminae that are permeable to gas but not to aqueous liquids can be formed, for example, from hydrophobic polymers solidified to porous solids. Suitable polymers are those that are solid, insoluble in aqueous fluids, particularly vaginal fluid, and readily formed into a layer, coating or lamina that does not dissolve, disperse into particulate form, or otherwise disintegrate upon contact with the sample. Examples of such polymers are ethyl cellulose, cellulose acetate and cellulose nitrate. Ethyl cellulose is particularly preferred. Alternatively, the indicator can reside in a hydrophilic water-permeable polymer that is covered by a hydrophobic, gas-permeable lamina.

Any indicator that changes color upon exposure to unprotonated amines, and preferably amines in a fluid specimen that would otherwise be acidic, may be used. Bromocresol green is one example of such an indicator, and may be used both here and in the pH test. Other examples are bromophenol blue, bromocresol purple, bromochlorophenol blue, nitrazine yellow, and various other indicators among those listed above.

The gas-releasing lamina and the gas-permeable indicator lamina are arranged in the test device such that the alkali in the gas-releasing lamina and the indicator in the gas-permeable lamina can be brought into contact only by the application of a fluid specimen. The laminae are arranged to permit the user to first contact the gas-releasing lamina with the specimen (preferably using a swab), and then to contact the gas-permeable indicator lamina with the same specimen, so that gas released in the specimen upon contact with the gas-releasing lamina will penetrate the gas-permeable lamina and thereby reach the indicator.

The substrate sheet for the amine test can be the same as that for the pH test, particularly when the two are included on a common test device. A coating can be applied to the substrate sheet for the same reasons and effects as disclosed above in the description of the pH test.

As further protection of the indicator in the gas-permeable lamina from liquid amines, an additional lamina that is permeable to gas but impermeable to liquid can be placed over the test indicator lamina. This protective or barrier lamina can be constructed of the same polymer used in the gas-permeable indicator lamina. Here again, ethyl cellulose is preferred.

The positive control indicator for the amine test is any indicator that will change color upon application of the sample regardless of the presence or absence of volatilizable amines in the sample. The color change may be due to the nonvolatile amines in the sample, or to the solid alkali in the gas-releasing lamina as the alkali is drawn into the sample by the applicator swab. The immobilizing matrix can be a hydrophilic polymer, and the same polymers cited above as preferred for use in the pH test can be used here as well. The indicator can be the same indicator used in the gas-permeable indicator lamina. One method of applying a positive control indicator that will change color regardless of whether the sample contains volatilizable amines is by incorporating the indicator in a matrix that is permeable to liquid rather than being permeable only to gas, and by placing the control in a position where it is not protected by the gas-permeable liquid-impermeable lamina.

While the present invention is susceptible to a wide range of configurations and embodiments, an understanding of the underlying concepts and principles of the invention and its novel aspects is best gained by a detailed review of specific embodiments. These are depicted in the drawings and described below.

DETAILED DESCRIPTIONS OF THE DRAWINGS

Figure 2:
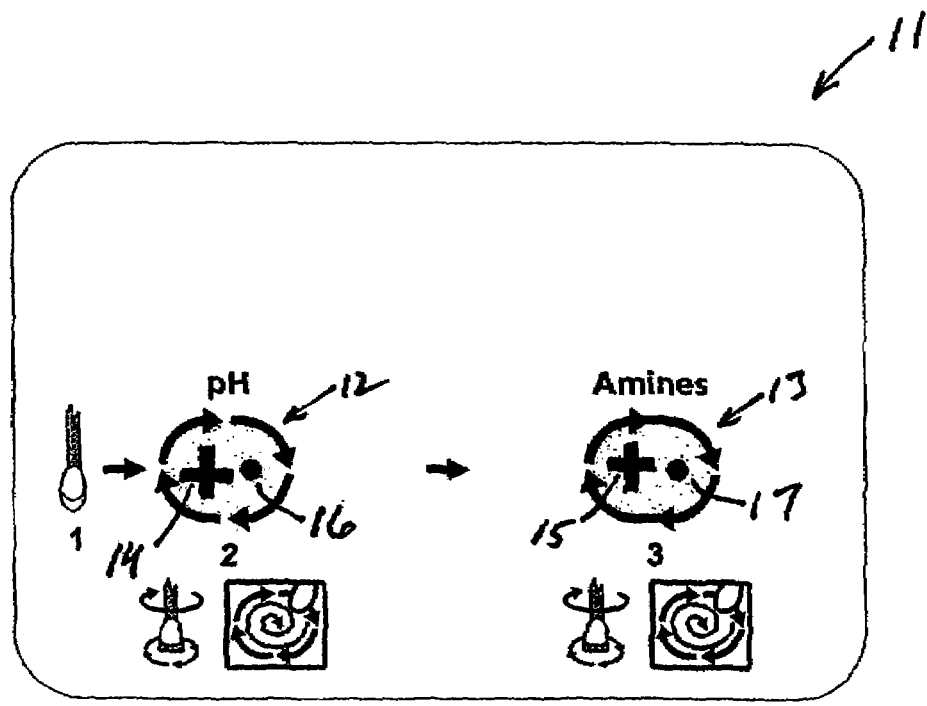
FIG. 2 is a plan view of the test device of FIG. 1 after a sample that is positive for both tests has been applied to both regions.

FIGS. 1 and 2 illustrate a single test device 11 containing separate test regions for a pH test and an amine test. The device is approximately the size of a common credit card (enlarged in the figure for ease of illustration) and is made of laminated plastic. FIG. 1 shows the device before any samples have been applied, while FIG. 2 shows the device after a sample has been applied to both test regions in succession and the test result in both cases is positive. The card includes a delineated area 12 of oval shape as the test region for application of a vaginal sample for the pH test and a second delineated area 13, also of oval shape, as the test region for application of a vaginal sample for the amines test. Within each test region is a test icon 14, 15, and a positive control icon 16, 17, the test icons appearing as plus signs and the positive control icons appearing as circular dots, all visible only in FIG. 2. Various indicia (not numbered) are printed on the surface of the device to guide the user, indicating that the sample should be collected on a cotton swab and that the swab should then be applied to the pH test region first and the amine test region second. The indicia also indicate that the swab should be applied in a circular motion in each case beginning at the periphery of the test region and moving toward the center in a spiral motion.

Figure 3:
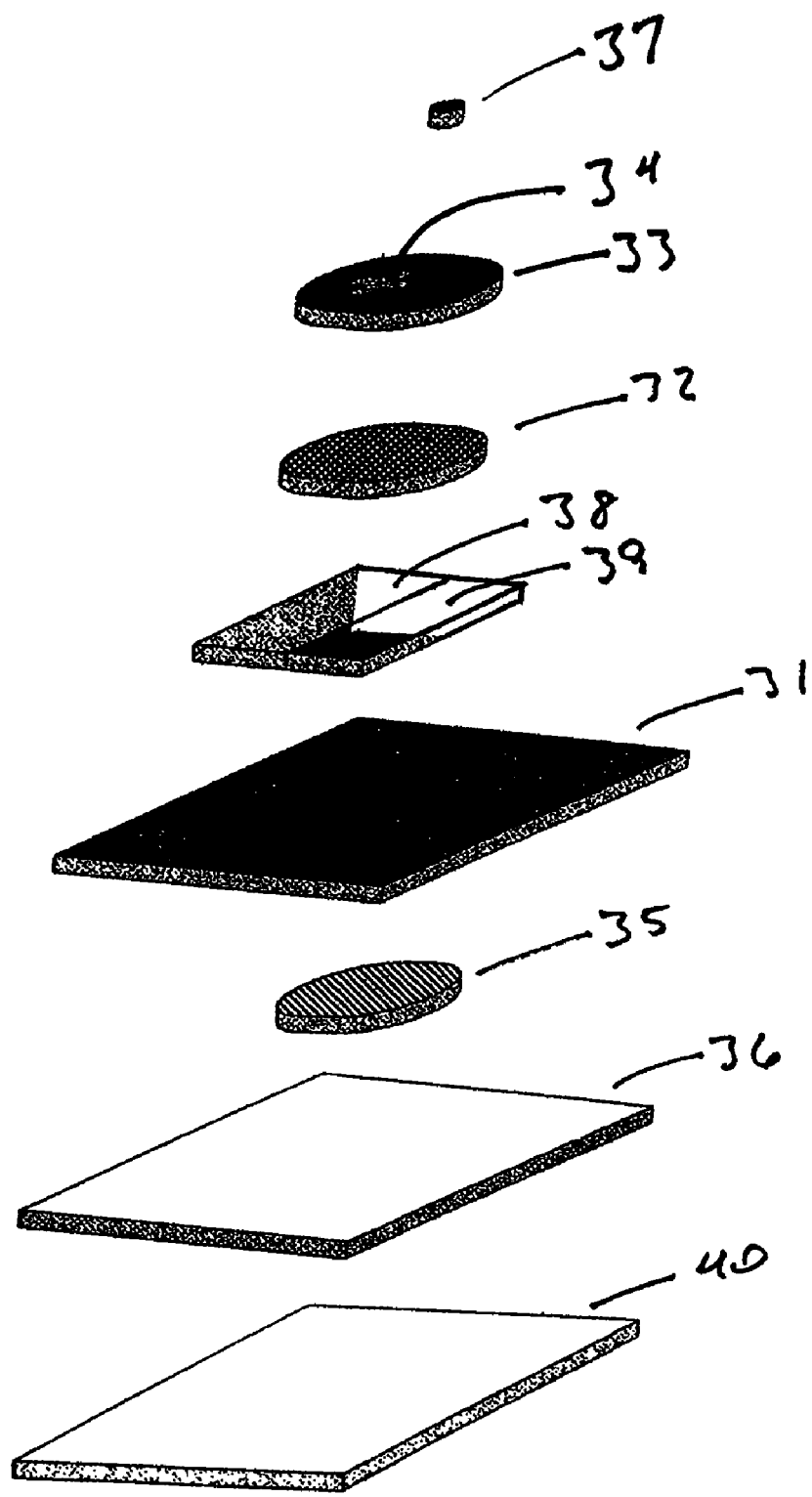
FIG. 3 is an expanded view in perspective of one arrangement of laminae forming the pH test region of the test device of FIGS. 1 and 2.

FIG. 3 depicts, in an expanded view, one example of an arrangement of laminae for the pH test portion of the device. The base over which the laminae are applied is the substrate sheet 31, which is a transparent solid sheet of nonporous material that is chemically inert to all substances coming in contact with it either during application of the laminae or in use in as the test is being performed. The test icon is created by the combination of an indicator lamina 32 and a transparent channeling lamina 33, the channeling lamina allowing liquid to pass only through a plus sign-shaped opening 34 in the channeling lamina. The pigment lamina 35 is applied to the underside of the substrate sheet 31, and when the pigment lamina is the same material as the indicator lamina 32, a layer of transparent polyamide 36 is applied to the underside of the pigment lamina. A positive control icon is applied as a separate lamina 37 above the channeling lamina 34. Additional, optional laninae include side-by-side coatings 38, 39, both transparent, over the substrate sheet (on the same side as the indicator lamina 32, channeling lamina 33, and control icon lamina 37), and an opaque white lamina 40 on the underside of the substrate sheet. The coatings 38, 39 are applied as solutions of different pH to help control the transition pH for the test indicator (the indicator lamina 32) at 4.7 and for the control reagents (the positive control 37) at 4.0. Optionally, as noted above, a single coating, preferably one that matches the pH of the indicator lamina 32, can be used in place of the two 38, 39 that are shown. The channeling lamina 33, indicator lamina 32, and pigment lamina 35 are all shaped as the oval test area 12 of FIGS. 1 and 2.

Figure 4:
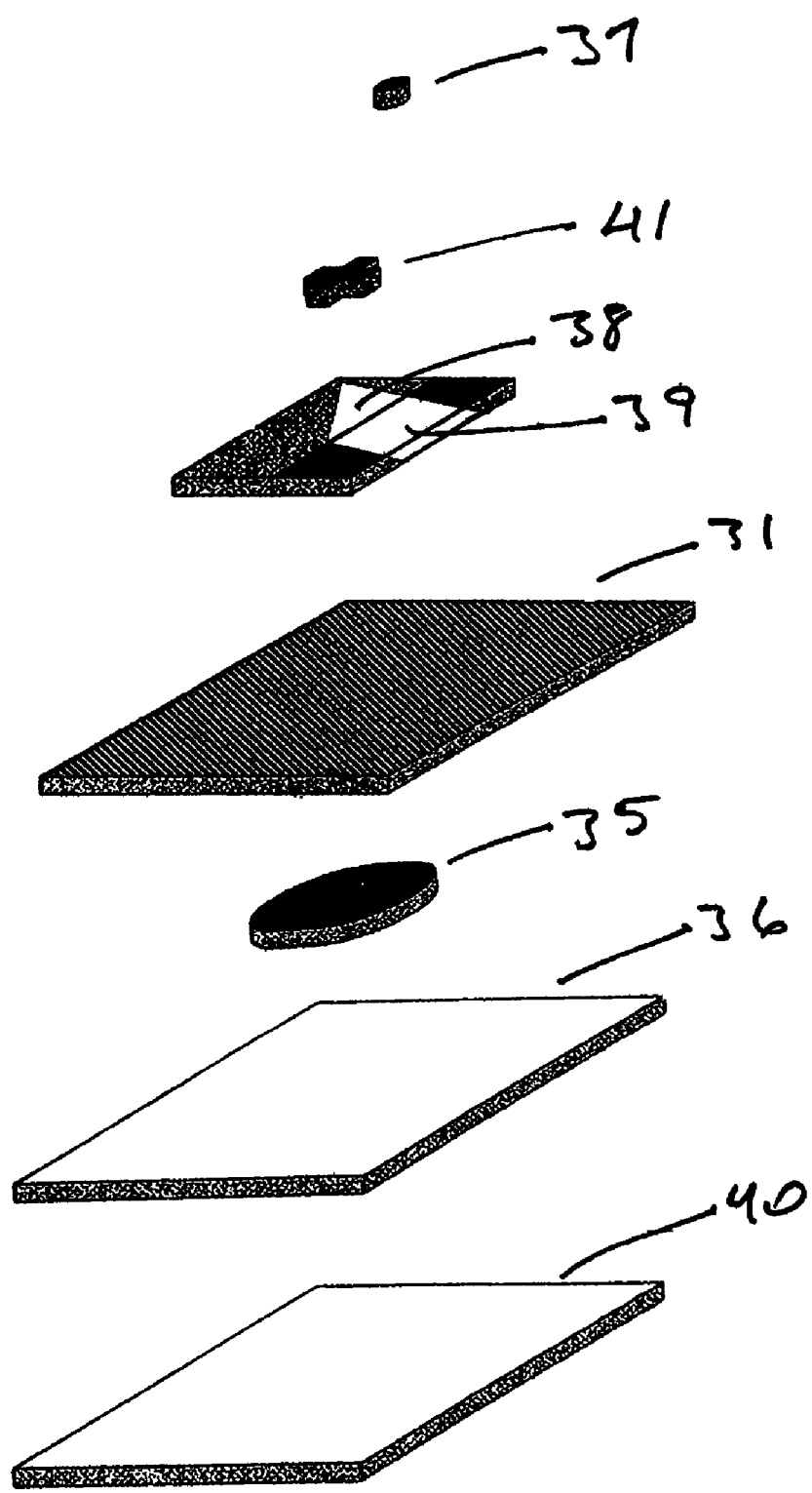
FIG. 4 is an expanded view in perspective of an alternative arrangement of laminae for the pH test region of the test device of FIGS. 1 and 2.

An alternative arrangement of laminae for the same pH test is depicted in FIG. 4. This arrangement differs from that shown in FIG. 3 as follows: the indicator lamina 32 of FIG. 3, which fills the oval of the test region, is replaced by a smaller, icon-shaped indicator lamina 41, and the channeling lamina 34 is eliminated entirely.

Examples of materials used in forming the various laminae shown in FIGS. 3 and 4 are as follows (all percents are by weight):

- the substrate sheet 31 is a sheet of MYLAR, 10 mils (0.001 inch, 0.00254 cm) in thickness
- the 38, 39 for enhanced control of the pH transition points are each ethyl cellulose applied as a 15% solution in n-propanol, the solution containing maleic acid in sufficient concentration to give the solution a pH of 2.2 for the test icon portion 38 and 4.6 for the positive control portion 39
- the adherence-promoting layer 36 is polyamide applied as a 20% solution of polyamide in a mixture of n-propanol acetate and n-propanol (50:30 weight ratio)
- the indicator laminae 32, 41 are yellow and transparent and each is applied as a solution of the following composition: 25.0% EUDRAGIT RL PO, 0.34% nitrazine yellow, 8.6% sorbitol (70% aqueous solution), 10.0% 2-ethoxy ethanol, 12.4% deionized water, and 43.66% 1-propanol
- the positive control lamina 37 is also yellow and transparent and is applied as a solution of the following composition: 25.0% EUDRAGIT RL PO, 0.17% nitrazine yellow, 0.30% bromocresol green, 8.6% sorbitol (70% aqueous solution), 30.0% 2-ethoxy ethanol, 12.4% deionized water, 0.65% 2-sulfobenzoic acid anhydride (for moisture resistance), and 22.8% 1-propanol
- the channeling lamina 33 is transparent ethyl cellulose, applied as a 15% solution in 30% n-propanol
- the pigment lamina 35 is an inert yellow ink, consisting of a mixture of 99.3% Pantone Yellow, 0.145% Process Blue, 0.29% Black, and 0.28% Warm Red
- the opaque white lamina 40 is CUSTAGLOSS® pure, opaque, white ink #1010

In a currently preferred embodiment, each oval test area is 0.391 inch (0.99 cm) in width and 0.2975 inch (0.756 cm) in height, the test indicators ("plus" signs) are bars 0.17 inch (0.43 cm) in length and 0.0553 inch (0.140 cm) in width, the positive control dots are 0.075 inch (0.190 cm) in diameter.

Figure 5:
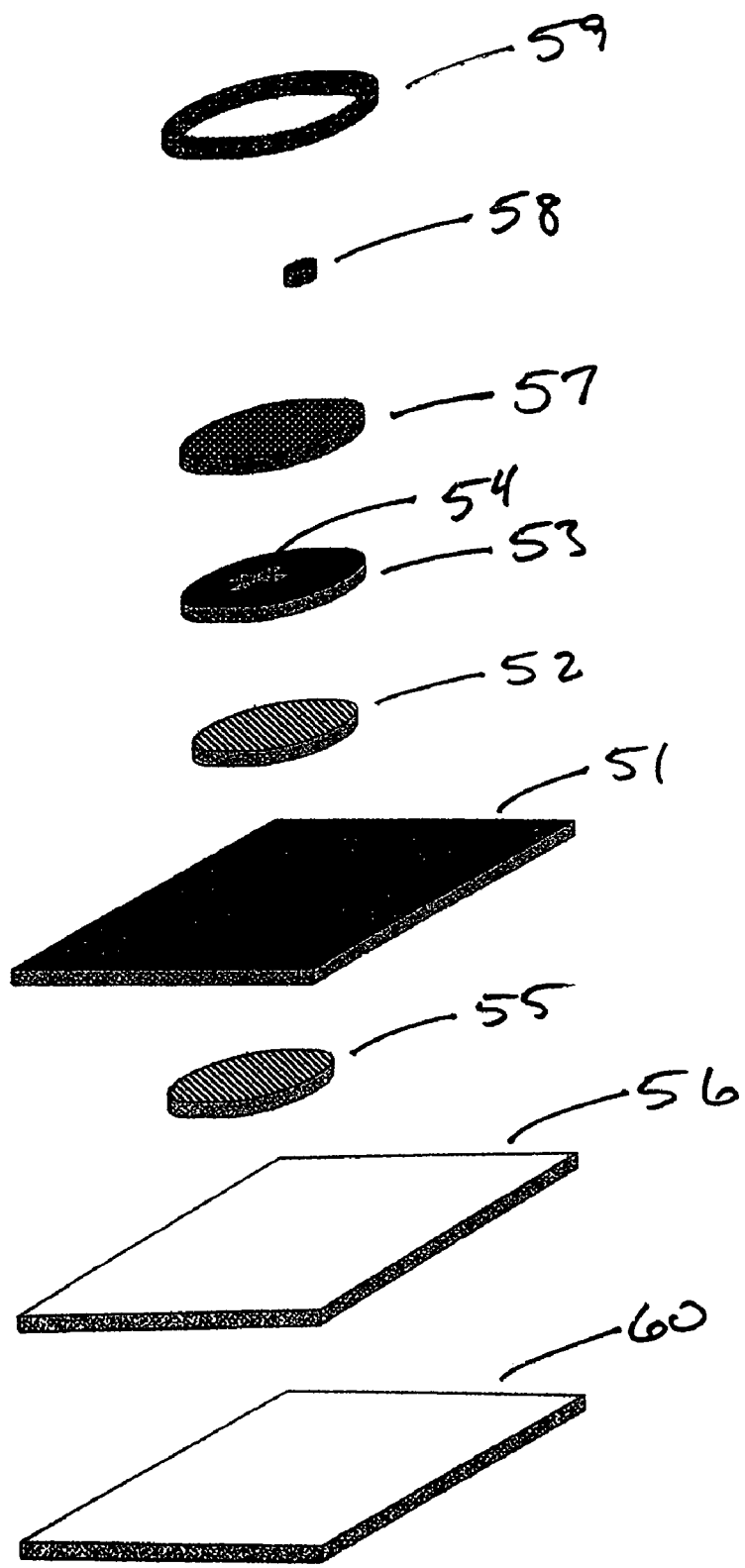
FIG. 5 is an expanded view in perspective of one arrangement of laminae forming the amines test region of the test device of FIGS. 1 and 2.

FIG. 5 depicts, in an expanded view, one example of an arrangement of laminae for the amine test portion of the device. Here, as in the pH test portion, the base over which the laminae are applied is a transparent solid substrate sheet 51 of nonporous material that is chemically inert to all substances coming in contact with it either during application of the laminae or in use in performing the test. The test icon is created by the combination of an indicator lamina 52 and a transparent channeling lamina 53, the latter having a plus sign-shaped opening 54 for the passage of liquid. On the underside of the substrate sheet 51 is a pigment lamina 55 applied over a layer of transparent polyamide 56, and when the pigment lamina is the same material as the indicator lamina 52, a layer of transparent polyamide 56 is applied to the underside of the pigment lamina. Above the channeling lamina 34 are a gas-permeable, liquid-impermeable lamina 57, a positive control icon 58, and a gas releasing lamina 59. An opaque white lamina 60 resides on the underside of the substrate sheet 51. The gas-permeable, liquid-impermeable lamina 57, channeling lamina 53, indicator lamina 52, and pigment lamina 55, are all shaped as the oval test area 13 of FIGS. 1 and 2.

Figure 6:
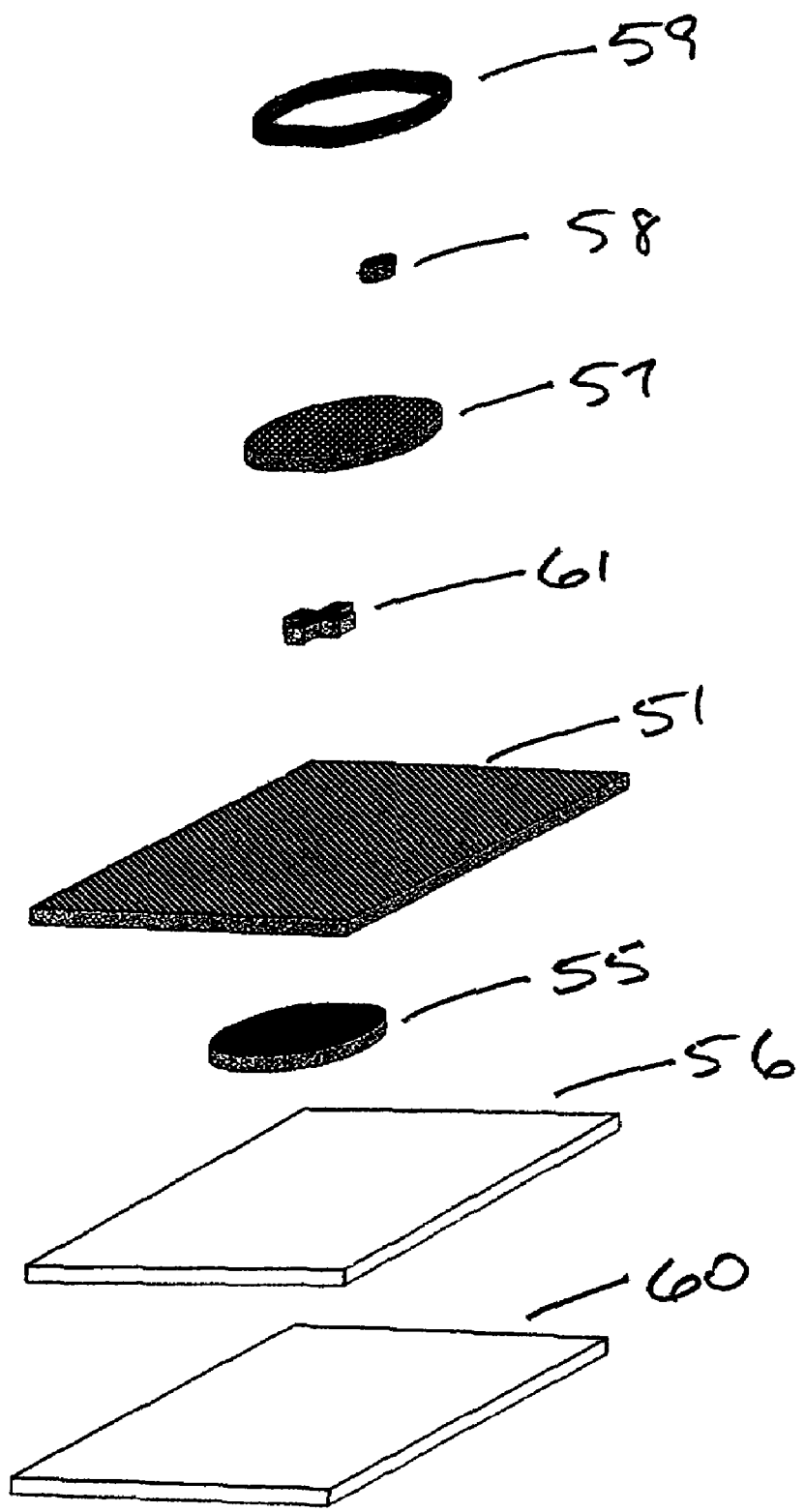
FIG. 6 is an expanded view in perspective of an alternative arrangement of laminae for the amines test region of the test device of FIGS. 1 and 2.

The alternative construction for the amine test is shown in FIG. 6. As in the alternative pH test, the test icon in this construction is formed from the indicator lamina alone rather than the combination of an indicator lamina and a channeling lamina. The differences between this arrangement and that of FIG. 5 are therefore the replacement of the indicator lamina 52 of FIG. 5, which fills the oval of the test region, by a smaller, icon-shaped indicator lamina 61, and the elimination of the channeling lamina 54. All other laminae are the same as their like-numbered counterparts in FIG. 5.

Examples of materials used in forming the laminae shown in FIGS. 5 and 6 are as follows (all percents are by weight):

- the substrate sheet 51 is a sheet of MYLAR, 10 mils (0.001 inch, 0.00254 cm) in thickness
- the indicator laminae 52, 61 are yellow and transparent and each is applied as a solution of the following composition: 1.8% bromocresol green, 12% ethyl cellulose, and 86.2% ethanol the channeling lamina 53 is clear polyamide, applied as a 20% solution in a mixture of n-propanol acetate and n-propanol (50:30 weight ratio)

the gas-permeable lamina 57 is colorless and transparent, and is applied as a 10% solution of ethyl cellulose in n-propanol the positive control lamina 58 is yellow and transparent and is applied as a solution of the following composition: 25.0% EUDRAGIT RL PO, 0.17% nitrazine yellow, 0.1% bromocresol green, 30.0% 2-ethoxy ethanol, 6.0% deionized water, 36.9% 1-propanol, and 2.0% 2-sulfobenzoic acid anhydride (for moisture resistance)

the pigment lamina 55 is an inert yellow ink, consisting of 99.3% Pantone Yellow, 0.145% Process Blue, 0.29% Black, and 0.28% Warm Red the gas-releasing lamina 59 is sodium aluminate applied as a solution containing 28% sodium aluminate, 18% polyethylene, 3% maltodextrin, and 51% deionized water the opaque white lamina 60 is CUSTAGLOSS® pure, opaque, white ink #1010

The dimensions of the plus sign and the positive control dot in this preferred embodiment are the same as those cited above for the pH test, plus the gas-releasing lamina which is formed of curved lines of solid alkali containing sodium aluminate in an amount equivalent by titration to 120-150 microliters of 0.01 N hydrochloric acid.

The invention is further illustrated by the following examples.

EXAMPLE 1

This example illustrates the benefit of the presence of a pigment lamina on the bottom surface of the substrate sheet in reducing the visibility of the incipient test icon formed on the top surface of the sheet. By "incipient" is meant that the observations were made on test device constructions that had not undergone any color change that would have resulted from reaction with an analyte. The device used was an amines test device as described above, and the test icon was formed by a channeling lamina placed over an indicator lamina covering the entire test region. The channeling lamina had an opening exposing a portion of the indicator lamina in the shape of the test icon. A construction having the configuration of FIG. 5 without the pigment lamina 55 and the opaque white lamina 59 was compared with a construction that lacked only the opaque white lamina 59. The difference between the two constructions was therefore the pigment lamina 55 which was absent in one and present in the other. The pigment used in the pigment lamina was the same material used as the indicator in the indicator lamina.

Visual examinations of the constructions were made without the application of any test samples or analytes. Thus the comparisons were made on the basis of the indicator prior to any color change. When the two constructions were compared by visual examination, the plus-sign lamina was faintly visible in the construction that did not contain the pigment lamina, the visibility due to the edges of the opening in the channeling lamina. This visibility was significantly less in the construction that contained the pigment lamina.

Two additional constructions were prepared, both containing the pigment lamina both lacking the opaque white lamina, but one containing a transparent protective polyamide lamina as an outer coating over the pigment lamina. Comparison of these two constructions, again by visual examination without the influence of any samples or analytes, revealed that the visibility of the icon outlines was reduced even more in the construction containing the transparent protective lamina.

EXAMPLE 2

This example illustrates the benefit of the presence of a transparent protective lamina underneath a pigment lamina on the bottom surface of the substrate sheet in reducing the visibility of the incipient test icon formed on the top surface of the sheet. The amines test device as described above was used here as well, and the test icon was formed by a plus-sign-shaped indicator lamina. Several constructions having configurations similar to that of FIG. 6 were prepared, including some with the opaque white lamina 59 and some lacking the opaque white lamina. Among each of these groups were constructions that also contained the polyamide layer and those that did not. In constructions that contained both the opaque white lamina and the polyamide layer, the polyamide was positioned between the pigment lamina and the opaque white lamina. As in Example 1, the pigment used in the pigment lamina in all cases was the same material used as the indicator in the indicator lamina.

Comparison of the various constructions by visual examination, without exposure to any samples or analytes, revealed that the polyamide layer reduced the visibility of the outlines of the plus-sign icon in both cases, i.e., both with and without the additional presence of the opaque white lamina.

EXAMPLE 3

This example illustrates the use of commercial ink combinations as the pigment lamina in place of the unchanged and protected indicator lamina. The commercial ink combinations were all chemically distinct from the indicator and not designed to change color upon exposure to any of the test materials under the conditions of the test. The advantage of using commercial ink combinations is that they can be formulated in a controlled manner to achieve a distinct color or color quality without requiring the lamina to change color.

The experiments in this example were conducted on the amines test device as described above, and the test icon was formed by a plus-sign-shaped indicator lamina. The same reagents and materials were used, except that the pigment lamina was substituted by each of four combinations of standard, primary-color printing inks, all commercially available and blended empirically to match as closely as possible the color of the plus sign-shaped indicator lamina. The four combinations were as follows (all percents are weight percents):

| Ink Combination No.: | 1 | 2 | 3 | 4 |
|---|---|---|---|---|
| Transparent white | 95.6% | 86.8% | 48.4% | 12.8% |
| Opaque white | 0.5% | 0.5% | 0% | 0% |
| Magenta | 0.25% | 0.5% | 0% | 0% |
| Pantone yellow | 3.65% | 1.20% | 51.5% | 86.1% |
| Rubin red | 0% | 0% | 0.18% | 0.7% |
| Black | 0% | 0% | 0% | 0.3% |

Each of the ink combinations was applied to a separate test laminate in one of two formats—the first as shown in FIG. 6 with the ink layer applied on the underside of transparent substrate sheet and the second with the ink layer applied on the upper side of the transparent substrate sheet immediately below the plus sign-shaped indicator lamina. Test solutions were prepared by dissolving solid trimethylamine hydrochloride at various concentrations in a solvent system consisting of 7% (by weight) propanol in distilled water. Concentrations of 1 mM and 5 mM were used, while the solvent system without trimethylamine was used in parallel tests as a control. The test solutions and the control were applied to laminates constructed according to both formats.

The visibility of the plus sign on each laminate was then determined by visual observation, as were any color changes in the background surrounding the plus sign. Prior to any application of the test solutions or control liquids, the outlines of the plus sign were almost completely invisible in both formats for all ink combinations. Upon application of the control liquids, the outlines of the plus sign remained almost completely invisible with all ink combinations except Combination No. 1. Upon application of the test solutions, the laminates of the first format (with the transparent substrate sheet positioned between the indicator lamina and the ink combination) produced better results than the laminates of the second format (with the indicator lamina and the ink combination on the same side of the substrate sheet). Laminates of the second format showed a slight color change in the ink combination, lessening the contrast between the plus sign and the background, while no such change was visible in laminates of the first format.

EXAMPLE 4

This example compares the performance of a pH test of the preferred formulation described above on test laminates in accordance with this invention with a COLORPHAST® pH test strip, manufactured by EM Science, Gibbstown, N.J., USA, currently sold for use by physicians. The test card was constructed with a plus sign-shaped indicator lamina of the preferred composition described above, and the pigment lamina was a commercial ink composition applied to the underside of the transparent substrate sheet. The ink combination was 99.3% Pantone Yellow, 0.14% Process Blue, 0.28% Black, and 0.28% Warm Red. Tests were performed on 472 vaginal fluid specimens.

Of the 472 specimens, 232 indicated a negative test result (i.e., pH<4.7) according to the COLORPHAST pH strip, and of these, 185 also indicated a negative result according to the test card of the present invention, or an agreement level of 79.7%. The positive test results (pH≧4.7) numbered 240 for the COLORPHAST strips, and of these, 185 tested positive on the test elements of the invention, or an agreement level of 91.7%. The overall accuracy was therefore 86%.

EXAMPLE 5

This example utilizes the traditional Amsel criteria to reconcile the results that were not in agreement in the tests performed in Example 4. As noted above, the Amsel criteria for bacterial vaginosis (BV) are based on a report by Amsel, R., et al., *Am. J. Med.* 74:14-22 (1983), which sets forth four criteria that collectively result in a diagnosis of BV: elevated pH (originally 4.5 or above, now 4.7 or above) of a vaginal fluid specimen, a "whiff" test (treatment of the specimen with alkali followed by an olfactory test to detect an amine odor), vaginal fluid homogeneity, and the presence of clue cells. To detect a positive result in the Amsel criteria, the elevated pH must be met, together with at least two of the remaining three criteria.

The 97 samples from Example 4 that were not in agreement were tested under the remaining three Amsel criteria (whiff test, vaginal fluid homogeneity, and the presence of clue cells). Of the 47 specimens that gave negative results by the COLORPHAST test strip and positive by the test laminate of the invention, only one was positive by the Amsel criteria. Of the 20 specimens that gave positive test results by the COLORPHAST test strip and negative by the laminate of the invention, 19 were negative according to the Amsel criteria. This represents a 99.5% agreement on the positive results, an 81.6% agreement on the negative results, and a 90% overall accuracy.

EXAMPLE 6

This example compares the performance of an amine test of the preferred formulation described above on laminates in accordance with this invention with the "whiff test" of the Amsel criteria. The laminates constructed with a plus sign-shaped indicator lamina of the preferred amine test composition described above, and the pigment lamina was a commercial ink composition applied to the underside of the transparent substrate sheet. The ink combination was 99.3% Pantone Yellow, 0.14% Process Blue, 0.28% Black, and 0.28% Warm Red. Both the test in accordance with the invention and the whiff test were performed on 464 vaginal fluid specimens.

Of the total number of specimens tested, 157 gave a positive response by the whiff test, and of these, 142 gave a positive result by the laminates of the invention, representing 90.4% positive agreement. Of the total number tested, 307 gave a negative result by the whiff test, and of these, 268 also gave a negative result by the laminates of the invention, representing an 87% agreement on the negative results. This amounts to an overall accuracy of 88.3%.

EXAMPLE 7

Amsel criteria were again used to reconcile the specimens that were not in agreement in the amine tests of Example 6. Here as well, if amines were detected because of vaginal infections, at least two of the other three Amsel criteria would be expected to be positive.

The 54 amine test samples that were not in agreement between the two tests were subjected to the remaining three Amsel criteria. Positive agreement rose to 94.2%, negative agreement rose to 88.7%, and overall accuracy to 91%.

EXAMPLE 8

This example compares the combined pH and amine tests of the present invention (using the laminates of the preceding examples) with the combined results of the COLORPHAST pH test and the standard whiff test of the Amsel criteria. Results using the laminates of the present invention were considered positive only when both the pH and the amine tests gave positive results, and negative in all other cases, i.e., when either or both of the pH and amine test gave a negative result. The reference tests were designated in the same manner—positive when both were positive and negative when any one or both were negative.

Of 464 vaginal fluid specimens, 149 specimens tested positive by the COLORPHAST/whiff tests and 140 tested positive on the laminates of the present invention. Likewise, 315 specimens tested negative by the COLORPHAST/whiff tests and 291 tested negative on the laminates of the present invention. Disagreement occurred in only 33 cases. This represents 94.0% positive agreement, 92.4% negative agreement, and an overall accuracy of 93.0%.

EXAMPLE 9

As with the individual test elements for the pH and amine tests, discrepancies in the results between the combined tests of the invention and the combined COLORPHAST/whiff tests were reconciled using the Amsel criteria to presumptively diagnose BV. Of the 24 specimens that were negative according to the COLORPHAST/whiff tests, only 9 were clinically positive for BV according to the Amsel criteria. Of the 9 specimens that were positive according to the COLORPHAST/whiff tests but negative according to the combined tests according to the present invention, 6 were clinically negative for BV according to the Amsel criteria. Thus, using the Amsel criteria to reconcile the disagreements between the results obtained from the different tests, positive agreement rose to 98.0%, negative agreement rose to 95.2% and overall accuracy rose to 96.1%.

EXAMPLE 10

This example illustrates the use of laminates of the present invention in conjunction with the two additional Amsel criteria for the determination of the presence or absence of BV. First, all women in the study group were tested for the all four criteria, using the COLORPHAST pH test strip for pH determination, the whiff test for amines, visual examination of the fluid for adherence and homogeneity, and microscopic examination for the presence of clue cells. The analysis was then repeated on the same group of women, using the same four criteria, but substituting the pH and amine test laminates of the present invention for the COLORPHAST and whiff tests.

The study group consisted of vaginal fluid specimens from 464 women. Based on the Amsel criteria results using the COLORPHAST and whiff tests, 156 (33.6%) of the women were classified as BV positive and 308 (66.4%) were classified as BV negative. Of the 156 positives, 152 were also classified positive using the laminates of the present invention (in conjunction with determinations of the vaginal fluid consistency and the presence of clue cells). Of the 308 negatives, 292 were also classified negative when the criteria were retested using the laminates of the present invention (in conjunction with the vaginal fluid consistency and presence of clue cells). This represents 97.4% positive agreement, 94.8% negative agreement and 95.6% overall agreement.

The 20 test results that were not in agreement were reconciled by a Gram stain test as an independent means of diagnosing BV, where a Gram stain score of 7 and above was considered BV positive. Of the 16 specimens that were BV negative by the Amsel criteria using the COLORPHAST and whiff tests and BV positive by the Amsel criteria when the laminates of the current invention were used, 7 were clinically positive for BV by the Gram stain test. Conversely, of the 4 specimens that were BV positive by the Amsel criteria when the COLORPHAST and whiff tests were used and BV negative when the laminates of the present invention were used, none were clinically negative by the Gram test. Thus, by reconciling the inconsistent results with the Gram stain test results, sensitivity (the percentage of positive test results relative to the positives by the Gram stain test) remained at 97.4%, specificity (the percentage of negative test results relative to the negatives by the Gram stain test) rose to 97.0% and overall agreement rose to 97.2%.

EXAMPLE 11

This example illustrates the use of the pH and amine tests performed on laminates in accordance With the present invention by themselves as combined test criteria for BV. Comparisons were made against the Amsel criteria (using the COLORPHAST strip for pH and the whiff test for amine), and the Gram stain test, in which a Gram stain score of 7 and above was considered BV positive, was used to reconcile results that were not in agreement between the laminates and the COLORPHAST/whiff tests. For pH and amine tests of the present invention, the diagnosis was considered positive only when both tests gave positive results. When one or both gave negative results, the diagnosis was considered negative.

Of the 464 vaginal specimens tested, 156 (33.6%) were positive by the Amsel criteria, and of these 156, 142 were also positive by the laminates of the present invention. Those testing negative by the Amsel criteria were 308 in number (66.4%), and of the 308, 286 were also negative by the laminates of the present invention. This indicates a sensitivity of 91.0%, a specificity of 92.9%, an overall accuracy of 92.2%.

The 36 test results that were not in agreement were then reconciled with the Gram stain test. Of the 22 that were BV negative by the Amsel criteria and positive by the tests of the present invention, 7 were BV positive by the Gram stain. Of the 14 that were BV positive by the Amsel criteria and negative on the laminates of the present invention, none were clinically negative by the Gram stain.

Thus, by reconciling non-agreeing test results with the Gram stain, 163 specimens were BV positive by the Gram-reconciled Amsel criteria, and of these, 149 were also positive by the laminates of the invention. Similarly, 301 specimens were negative by the Gram-reconciled Amsel criteria, and of these, 286 were also negative by the laminates of the invention. This raised the sensitivity to 91.4%, the specificity to 95.0%, and the accuracy to 93.8%.

EXAMPLE 12

This example illustrates the use of the amine test performed on a test card in accordance with the present invention as a test for clue cells. The same amine test materials and laminate configuration used in Example 6 above were used in this example. Comparisons were made against microscopic detection of clue cells, and the Gram stain was used to reconcile results that were not in agreement between the test card conclusions and the microscopic evaluation. The microscopic detection for clue cells was considered positive when clue cells constituted more than 20% of the vaginal epithelial cells present in a vaginal fluid specimen. As in the preceding examples, an amine test on a laminate of the present invention was considered positive when a visible plus sign appeared and negative when no plus sign appeared.

Of the 464 vaginal fluid specimens tested in the preceding examples, 160 were interpreted as positive for clue cells by microscopy. Of these 160 clue cell positive specimens, 140 were also positive by the amines test of the present invention. Specimens testing negative for clue cells by microscopy were 304 in number, and of these, 263 were also negative by the amine test of the present invention. This indicates a positive agreement of 87.5%, a negative agreement of 86.5% and an overall accuracy of 87%.

The 61 test results that were not in agreement were then reconciled by the Gram stain test. Of 41 specimens that were clue cell negative by microscopy and positive by the amines test of the present invention, 4 were clinically positive for BV by Gram stain analysis. Similarly, of the 20 specimens that were positive by microscopy criteria and negative by the amine test of the present invention, 6 were clinically positive for BV by Gram stain testing. Thus, by reconciliation of the above data using Gram stain scores, the positive agreement was raised to 91.1%, the negative agreement was raised to 87.9%, and the overall accuracy was raised to 89%.

EXAMPLE 13

This example demonstrates the effectiveness of an amine test in accordance with the present invention as a test by itself for bacterial vaginosis, by comparing the results of the amine test with the results of a standard bacterial vaginosis test performed using the Amsel criteria. The test materials and configuration representing the present invention were the same as those used in Example 6 above. Both the tests according representing the invention and the Amsel criteria tests were performed on the same 464 vaginal fluid specimens.

Of the total number of specimens tested, 156 specimens tested positive by the Amsel criteria, and 142 of these tested positive as well by the laminates of the invention, representing 91.0% sensitivity. Of the total number tested, 308 tested negative by the whiff test, and of these, 269 also tested negative by the laminates of the invention, representing an 87.3% negative agreement. Overall accuracy was 88.6%. This indicates that bacterial vaginosis can be diagnosed on the basis of the amine test alone with a high degree of accuracy.

EXAMPLE 14

The specimens in the above example that were not in agreement were reconciled by Gram stain tests. The amine test samples that were not in agreement between the tests were 53 in number, and with the Gram stain analysis, sensitivity rose to 91.4%, specificity rose to 89.4% and overall accuracy to 90.0%. Hence, the amines test laminates in accordance with this invention provided equivalent accuracy for the detection of BV to that determined by means of the four Amsel Criteria.

The foregoing is offered primarily for purposes of illustration. It will be readily apparent to those skilled in the art that the configurations, dimensions, reagents and other materials, procedural steps and other parameters of this invention can be further modified or substituted in various ways without departing from the spirit and scope of the invention.

What is claimed is:

1. A test device for analyzing a liquid sample for the presence of a selected analyte, said test device comprising: a light-transmitting, liquid-impermeable substrate sheet coated on one side with an analyte indicator lamina and on an opposing side with a pigment lamina, said analyte indicator lamina reactive with said analyte in a reaction producing a color change in said analyte indicator lamina, and said pigment lamina being of the same composition as that of said indicator lamina, so that said pigment lamina is of a color visually indistinguishable from that of said analyte indicator lamina when said analyte indicator lamina is in unreacted condition, said pigment lamina fully covering a selected test region on said substrate, and means for restricting said color change in said analyte indicator lamina to a restricted area within, and smaller than, said test region, thereby leaving adjacent areas within said test region unchanged.

2. The test device of claim 1 wherein said analyte indicator lamina fully covers said selected test region, and said means for restricting said color change is a channeling lamina overlying said analyte indicator lamina, said channeling lamina having an opening therein to expose said restricted area of said analyte indicator lamina.

3. The test device of claim 2 wherein said channeling lamina is transparent.

4. The test device of claim 1 wherein said means for restricting said color change is the application of said analyte indicator lamina only to said restricted area, leaving said adjacent areas free of said analyte indicator lamina.

5. The test device of claim 1 wherein said substrate sheet is transparent.

6. The test device of claim 1 wherein said restricted area is in the shape of a plus sign, and said adjacent areas surround said plus sign contacting all boundaries thereof.

7. The test device of claim 1 further comprising a control indicator lamina that is reactive with said sample in a reaction producing a color change in said control indicator lamina regardless of whether said analyte is present in said sample, and means for restricting said color change in said control indicator lamina to a restricted area separated from said restricted area of said color change in said analyte indicator lamina.

8. The test device of claim 1 wherein the side of said pigment lamina opposite said substrate sheet is coated with an opaque white lamina.

9. The test device of claim 1 wherein said analyte indicator lamina is a hydrophilic fluid-permeable polymer impregnated with a compound containing an ionizable phenol group and a negatively charged group, said polymer containing quaternary ammonium groups in sufficient quantity to immobilize said compound against diffusion when wetted with an aqueous liquid sample and to cause said reaction to occur at a pH equal to or greater than a transition point within the range of 4.6 to 4.8.

10. The test device of claim 9 wherein said compound is a member selected from the group consisting of bromophenol blue, bromochlorophenol blue, bromocresol green, bromocresol purple, bromothymol blue, brilliant yellow, and nitrazine yellow, and said quaternary ammonium groups are tri-($C_1$-$C_4$ alkyl)ammonium groups.

11. The test device of claim 9 wherein said compound is nitrazine yellow and said quaternary ammonium groups are trimethylammonium groups.

12. The test device of claim 1 wherein said analyte indicator lamina is a matrix of material permeable to gas but impermeable to aqueous liquids, impregnated with an compound that undergoes a color change upon contact with amines, and said test device further comprises a lamina of solid alkali.

13. The test device of claim 12 wherein said compound is a member selected from the group consisting of bromocresol green, bromophenol blue, bromocresol purple, bromochlorophenol blue, and nitrazine yellow.

14. A test device for analyzing a liquid sample for the presence of a selected analyte, said test device comprising: a light-transmitting, liquid-impermeable substrate sheet coated on one side with an analyte indicator lamina and on an opposing side with a pigment lamina, said analyte indicator lamina reactive with said analyte in a reaction producing a color change in said analyte indicator lamina, and said pigment lamina being of the same composition as that of said indicator lamina, so that said pigment lamina is of a color visually indistinguishable from that of said analyte indicator lamina when said analyte indicator lamina is in unreacted condition, said pigment lamina fully covering a selected test region on said substrate, and means for restricting said color change in said analyte indicator lamina to a restricted area within, and smaller than, said test region, thereby leaving adjacent areas within said test region unchanged;

and further comprising a control indicator lamina that is reactive with said sample in a reaction producing a color change in said control indicator lamina regardless of whether said analyte is present in said sample.

15. The test device of claim 14 comprising a means for restricting the control indicator color change in said control indicator lamina to a restricted area separated from said restricted area of said color change in said analyte indicator lamina.

16. The test device of claim 15 wherein said analyte indicator lamina fully covers said selected test region, and said means for restricting said color change in said analyte indicator lamina is a channeling lamina overlying said analyte indicator lamina, said channeling lamina having an opening therein to expose said restricted area of said analyte indicator lamina.

17. The test device of claim 16 wherein said channeling lamina is transparent.

* * * * *